United States Patent [19]

Weber et al.

[11] Patent Number: 4,837,070
[45] Date of Patent: Jun. 6, 1989

[54] TAPE BACKING SUBSTRATE

[75] Inventors: Robert E. Weber, Marietta; Bruce G. Stokes, Woodstock, both of Ga.

[73] Assignee: Kimberly-Clark Corporation, Neenah, Wis.

[21] Appl. No.: 248,342

[22] Filed: Sep. 20, 1988

Related U.S. Application Data

[63] Continuation of Ser. No. 128,767, Dec. 4, 1987, abandoned.

[51] Int. Cl.$^4$ ............................................. B32B 5/14
[52] U.S. Cl. .................................... 428/172; 264/238; 264/500; 427/411; 427/412; 427/413; 428/171; 428/284; 428/286; 428/290; 428/343; 428/354; 428/356
[58] Field of Search ............... 428/172, 171, 284, 286, 428/290, 343, 354, 356; 427/411, 412, 413; 264/238, 500

[56] References Cited

U.S. PATENT DOCUMENTS

| | | | |
|---|---|---|---|
| 3,466,187 | 9/1969 | Heinemann | 117/122 |
| 3,482,683 | 12/1969 | Desnoyers | 206/59 |
| 3,797,495 | 3/1974 | Schmidt | 128/287 |
| 3,928,690 | 12/1975 | Settineri et al. | 428/40 |
| 4,173,676 | 11/1979 | Asakura et al. | 428/332 |
| 4,188,439 | 2/1980 | Asakura et al. | 428/215 |
| 4,188,442 | 2/1980 | Asakura et al. | 428/216 |
| 4,202,925 | 5/1980 | Dabroski | 428/219 |
| 4,287,255 | 9/1981 | Wong et al. | 428/343 |
| 4,302,500 | 11/1981 | Flora | 428/284 |
| 4,307,145 | 12/1981 | Goldman | 428/247 |
| 4,358,494 | 11/1982 | Akimoto et al. | 428/40 |
| 4,693,920 | 9/1987 | Agarwal et al. | 428/434 |

OTHER PUBLICATIONS

Cellulose Chemistry and its Applications, T. P. Nevell and S. Haig Zeronian (editors), John Wiley & Sons, New York, Chapter 1.

Primary Examiner—Marion E. McCamish
Attorney, Agent, or Firm—Patrick C. Wilson

[57] ABSTRACT

There is disclosed a cloth-like tape substrate. The substrate is made from an essentially unbonded cellulose web having a breaking length between about 0.71 km and 2.66 km which is saturated with a soft rubber-like polymer, coated with a low stiffness polymer, and then embossed. The unbonded web is formed from at least 25% by weight of pulp having $R_{10}$ values greater than 94%. The soft rubber-like polymer has a glass-transition temperature between −50° C. and 0° C. and the low stiffness polymer coating has a tensile modulus less than 1,000 MPa.

21 Claims, 5 Drawing Sheets

TAPE BACKING SUBSTRATE

This is a continuation of co-pending application Ser. No. 128,767 filed on Dec. 4, 1987, now abandoned.

BACKGROUND OF THE INVENTION

This invention relates generally to substrate backings for tapes, and more particularly concerns a tape backing substrate which is flexible, strong, and has the look and feel of cloth.

It is well known in the art to use paper based tapes to secure disposable diapers to infants. Such diaper tapes are subjected to a complex variety of stresses, regardless of the mechanism of these stresses and the failure that may occur to the tape, it is known that such paper based tapes that have a tensile strength of about 11 kg/25 mm and an elongation value of above about 10% (TAPPI Test Method T404-OS-61) have adequate strength for use on diapers. Generally such tape substrates have a basis weight range from 80 to 200 g/m$^2$ and this is in agreement with Schmidt U.S. Pat. No. 3,797,495.

In the case of this invention, although cellulose fiber is used as in paper based tapes, the combining of unbonded cellulose with rubber-like polymers allows the stress forces to distribute over much larger areas and the tape both in looks and functional characteristics is more like a cloth tape.

Schmidt U.S. Pat. No. 3,797,495 discloses a pressure sensitive adhesive tape for diapers having a substrate consisting of a kraft base with a basis weight of 130 g/m$^2$ which has been beater treated with nitrile rubber. In another example, the tape substrate has a basis weight of 88 g/m$^2$ and is made from a bleached kraft fiber saturated with 50 parts per 100 parts of fiber of a combination of 100 parts of a polyacrylate emulsion and one part of an alkylketene dimer sizing agent. While such tapes function adequately for holding diapers on infants, the tapes substrate has the flex and feel of paper.

Desnoyers U.S. Pat. No. 3,482,683 discloses a pressure sensitive tape consisting of a paper substrate laminated with a film comprising a hypermolecularly oriented linear crystalline polyolefin film. The combination of the crystalline film and paper provide a bundling tape having a relatively low longitudinal extensibility and high resistance to cross-wise tearing forces. The primary strength of the substrate is the oriented film and not the secondary paper layer.

Hienemann et. al. U.S. Pat. No. 3,466,187 discloses a pressure sensitive tape formed from a cellulosic sheet containing 5% to 20% asbestos fibers and impregnated with an elastomeric composition of carboxylated/butadiene/acrylonitrile copolymer latex and coated on at least one side with a pressure sensitive adhesive. Particularly, the nitrile latex used is characterized as a medium hardness latex. The paper substrate contains a major portion of cellulose fiber and is prepared by methods known in the art except for the addition of 5% to 20% by weight of asbestos fibers. In one example, the paper consisted of 10% by weight of asbestos fibers, 80% northern kraft and 10% chemically-curled northern kraft fibers. Such paper substrate has the look and feel of paper.

One of the esthetic drawbacks of conventional disposable diapers is the plastic backing on the diapers which may be objectionable for several reasons. First, esthetically the plastic backing feels uncomfortable when a person is holding an infant who is wearing such a diaper. Second, the plastic film material does not breathe, and therefore, moisture remains trapped inside of the diaper where it can cause diaper rash. With the development of new materials which are impervious to liquid, permeable to air, and have the look and feel of cloth for disposable diapers, it is desirable to have a diaper tape which itself has the look and feel of cloth so that it esthetically compliments the cloth-like materials now being incorporated into new diaper products. In general, the tapes of the prior art that have sufficient strength to perform as diaper tapes, do not have the esthetic qualities of cloth which are desirable.

SUMMARY OF THE INVENTION

It is therefore an object of the present invention to provide a tape backing substrate which is flexible, has the look and feel of cloth, and has the necessary strength and durability to perform as a diaper tape.

In order to achieve the foregoing objective, the tape backing substrate is initially formed from an essentially unbonded cellulose web which is comprised of pulp fibers with $R_{10}$ values equal to or greater than 94 percent. This essentially unbonded cellulose web has very little fiber-to-fiber bonding such as is typically found in papers. The cellulose web is then saturated with a soft rubber-like polymer having a glass-transition temperature (Tg) between about −50° C. and 0° C. The resulting saturated cellulose web has primarily fiber-rubber-fiber bonds and essentially no direct cellulose fiber-cellulose fiber bonds which, because of the softness of the rubber, produces a web that is soft and cloth-like in feel. The fiber-rubber-fiber bond act like hinges between the individual fibers and this is what is believed contributes to the cloth-like feel of the web.

After the web has been saturated with the soft rubber-like polymer, the substrate is coated with a low-stiffness thermoplastic polymer to produce a flexible cloth-like tape substrate. By coating the rubber saturated cellulose web with a low-stiffness thermoplastic polymer such as low density polyethylene, polyethylene acrylic acid, or polyethylene vinyl acetate to a thickness of from 0.006 to 0.050 mm and embossing a fabric-like pattern on the outside surface, the resulting tape substrate not only has the look and feel of cloth, but also the necessary strength and durability to serve adequately as diaper tape.

Other objects and advantages of the present invention will become apparent upon reading the following detailed description and upon reference to the drawings.

DETAILED DESCRIPTION OF THE INVENTION

While the invention will be described in connection with a preferred embodiment, it will be understood that we do not intend to limit the invention of that embodiment. On the contrary, we intend to cover all alternatives, modifications, and equivalents as may be included within the spirit and scope of the invention as defined by the appended claims.

Figure 9:
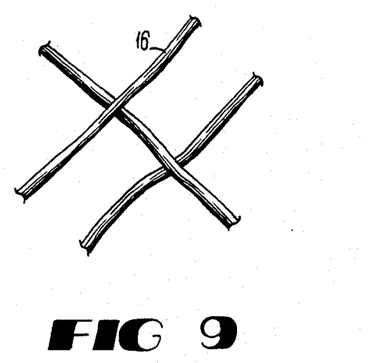
FIG. 9. is an enlarged portion of the tape substrate showing the unbonded fibers.
Figure 10:
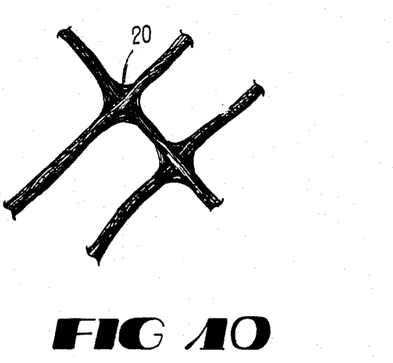
FIG. 10 is an enlarged portion of the tape substrate showing the fiber-rubber-fiber bonds of the saturated substrate.

Turning to FIGS. 1, 2 and 9 through 11, there is shown a tape substrate 10 comprising a cellulose web 12 and thermoplastic coating 14 and 15. The cellulose web 12 consists of cellulose fibers 16 which are bonded to each other by a soft rubber-like polymer 18 to form fiber-rubber-fiber bonds 20 instead of fiber-to-fiber bonds (FIGS. 9 and 10). At least 25% by weight of the cellulose fibers 16 in the web 12 have $R_{10}$ values of 94% or greater. Most preferably the amount of cellulose with an $R_{10}$ value of 94% or greater is 50 to 100% of the cellulose fiber in the substrate. $R_{10}$ defines the portion of the cellulose fibers 16 that are insoluble in 10% sodium hydroxide using ASTM method D 1696. $R_{10}$ fibers consist of undamaged long chain alpha cellulose.

The material 18 which forms the fiber-rubber-fiber bonds 20 is a soft rubber-like polymer which has a glass-transition temperature (Tg) between $-50°$ C. and $0°$ C. The transition temperature is determined by DTA or DSC techniques in accordance with ASTM D-3418. Such soft rubber-like polymers 18 may include natural rubber, nitrile rubber, styrene butadiene rubber, polyacrylates, ethylene vinylacetates, and other related soft polymers that have rubber-like properties.

Figure 1:
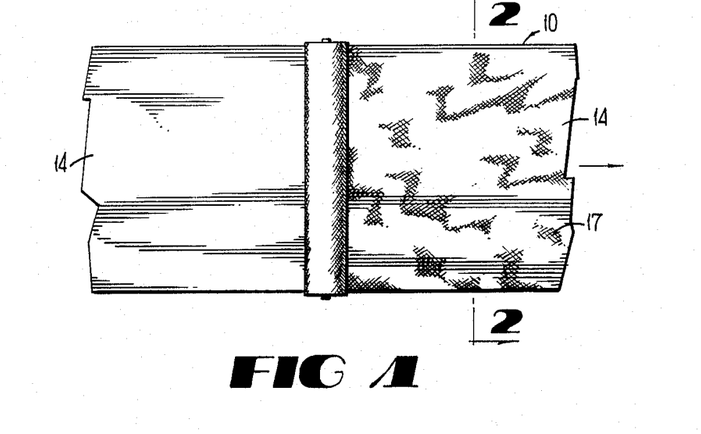
FIG. 1 is a top plan view of a tape substrate of the present invention.
Figure 2:
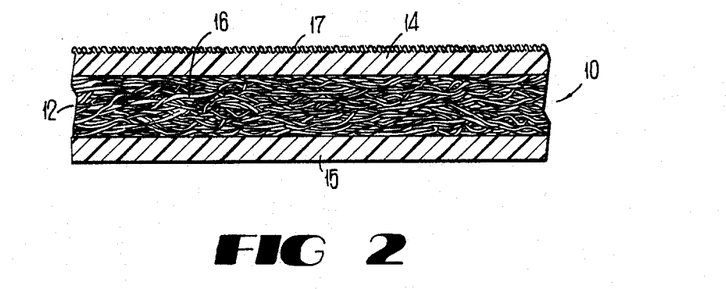
FIG. 2 is a cross section view of the tape substrate of the present invention as seen along line 2—2 of FIG. 1.

The thermoplastic coating 14 and 15 consist of a low-stiffness thermoplastic polymer. Thermoplastic polymers suitable for such coatings may include low density polyethylene, polyethylene vinyl acetate, polyethylene acrylic acid, and other copolymers of polyethylene. The thermoplastic coatings 14 and 15 are each 0.006 mm to 0.05 mm in thickness, and coating 14 has a fabric-like pattern 17 embossed on its outside surface to create the further impression of a fabric instead of a plastic substrate.

The advantageous features of the substrate 10 including its strength and cloth-like characteristics result from the method by which the substrate 10 is made. The cellulose web 12 is formed by a conventional wet paper making process using cellulose pulp having $R_{10}$ values equal to or greater than 94% by weight. The resulting cellulose web is essentially unbonded as there is very little fiber-to-fiber bonding between the cellulose fibers (FIG. 9). The lack of fiber-to-fiber bonding in the cellulose web 12 is shown by the tensile strength of the un-bonded web, i.e., an unbonded web has a lower tensile strength than a fiber-to-fiber bonded web. The tensile strength for the unbonded web of the present invention is measured by the breaking length of the web which is the average of the machine direction and cross-machine direction tensile strengths in kilograms per meter (kg/m) divided by the basis weight of the web in kilograms per meter square (kg/m$^2$) to produce a paper characteristic expressed as a unit length using TAPPI method T 494-OM-81. Simply stated, the breaking length is the length of a sheet of paper that when suspended from one end will break under its own weight. In connection with the present invention, the useful range of breaking lengths is 0.71 to 2.66 km with the preferred range being from 0.89 to 1.77 km. Such a range of breaking lengths is substantially less than the breaking lengths of the cellulose webs that are generally used in connection with making rubber saturated papers. In general, most cellulose webs used in making rubber saturated papers have breaking lengths above 2.84 km and as high as 6.20 km.

Cellulose webs with long breaking lengths are inherently stronger than lower breaking length webs due to the higher degree of fiber-to-fiber bonding. However, these higher strength webs tend to be too rigid because of the higher fiber-to-fiber bonding. Consequently, a lower breaking length web has been incorporated into the present invention and then subsequently modified with rubber-like polymer binder and thermoplastic coatings.

Figure 3:
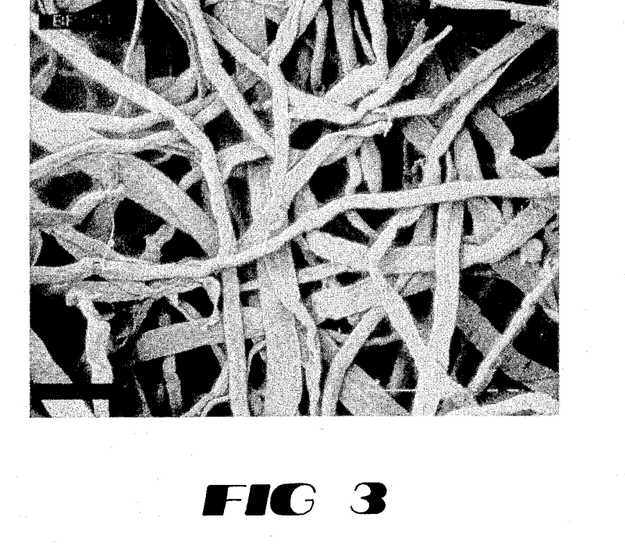
FIG. 3 is a micro-photograph of the surface of an unbonded cellulose web used in accordance with the present invention magnified to 200x.
Figure 4:
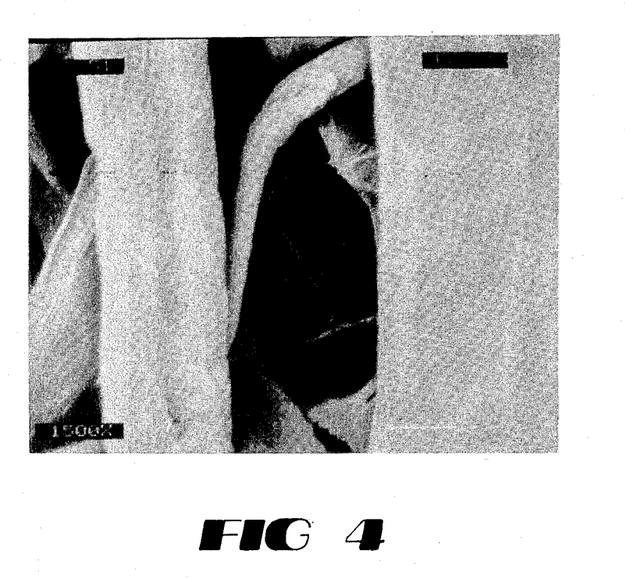
FIG. 4 is a micro-photograph of the unbonded cellulose web of FIG. 3 magnified to 1500x.
Figure 5:
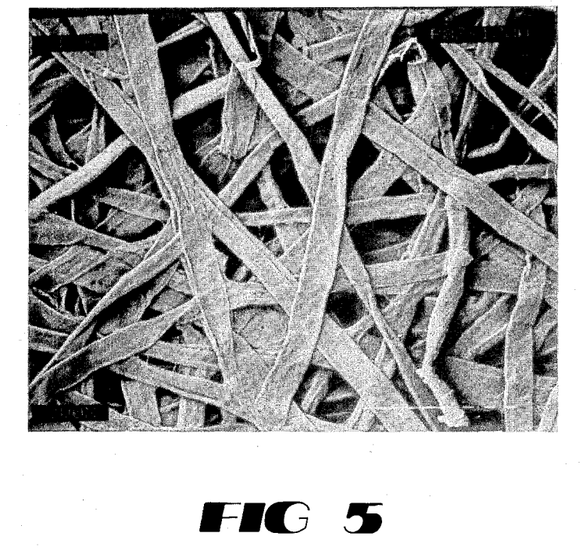
FIG. 5 is a micro-photograph of a bonded cellulose web which is not suitable for use in accordance with the present invention magnified to 200x.
Figure 6:
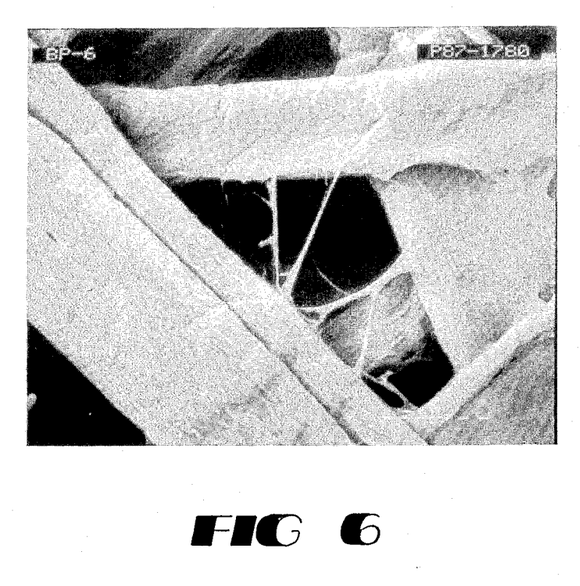
FIG. 6 is a micro-photograph of the bonded cellulose web of FIG. 5 magnified to 1500x.
Figure 7:
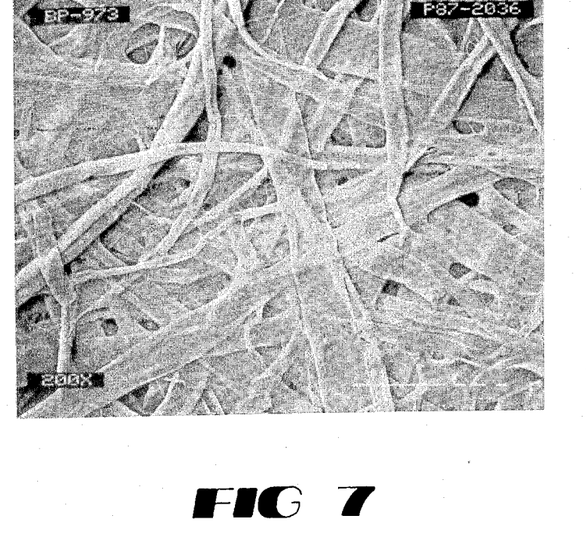
FIG. 7 is a micro-photograph of another bonded cellulose web which is not suitable for use in accordance with the present invention magnified to 200x.
Figure 8:
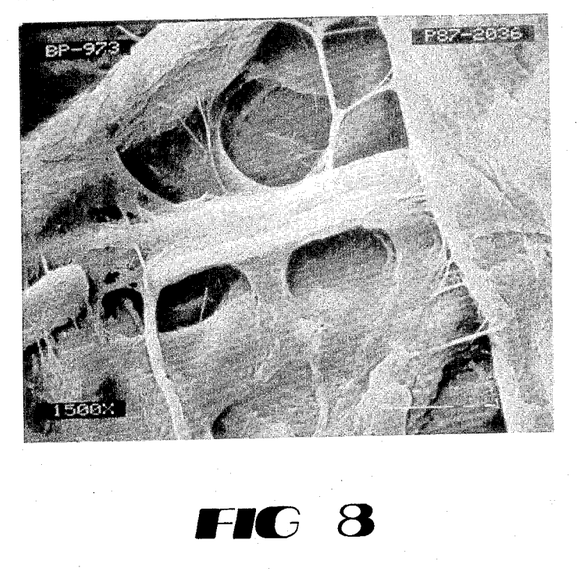
FIG. 8 is a micro-photograph of the bonded cellulose web of FIG. 7 magnified to 1500x.

FIGS. 3 and 4 illustrate an essentially unbonded cellulose web which is useful in carrying out the present invention. By contrast, FIGS. 5-8 illustrate two bonded webs which are typical of the cellulose webs used in making conventional rubber saturated papers, but which are not useful in connection with the present invention due to the degree of fiber-fiber bonding. Particularly, the unbonded cellulose web of FIGS. 3 and 4 has a breaking length of 0.71 km, and as can be seen in the microphotographs, there is very little fiber-to-fiber bonding within the cellulose web. By contrast, the cellulose web in FIGS. 5 and 6 has a breaking length of 3.10 km (a higher tensile strength than the range of the present invention), and as can be seen from the microphotographs, there is some fiber-to-fiber bonding between the fibers (FIG. 6). By further contrast, the cellulose web in FIGS. 7 and 8 has a relatively high degree of fiber-to-fiber bonding with a resulting average breaking length of 6.20 km. The microphotographs, particularly FIG. 8, show a high degree of fiber-to-fiber bonding between the cellulose fibers in the web and is typical of rubber saturated cellulose tapes which do not have the cloth-like feel of the present invention.

Because the cellulose web 12 shown in FIGS. 3 and 4 does not have a high degree of fiber-to-fiber bonding and is bulky, the resulting web is low in tensile strength, and because of its bulk, it does not have a high degree of flexibility. Consequently, such bulky sheets are not suitable without further modification through saturation and compression to create fiber-rubber-fiber bonding.

After the unbonded cellulose 12 has been formed by a conventional wet paper making process, the dried unbonded cellulose web 12 is then saturated with a soft rubber-like polymer. To make this type of product, the amount of saturant with the soft rubber is generally in the range of 40 to 80 parts dry rubber to 100 parts fiber. The resulting saturated cellulose web 12 has fiber-rubber-fiber bonds 20 which are illustrated in greater detail in FIGS. 10 and 11. Because the rubber that is used is a soft rubber, the fiber-rubber-fiber bonds 20 themselves are soft and flexible thereby allowing the fibers to flex at the bonding points like a hinge. The result is that the web 12 remains flexible.

Figure 11A:
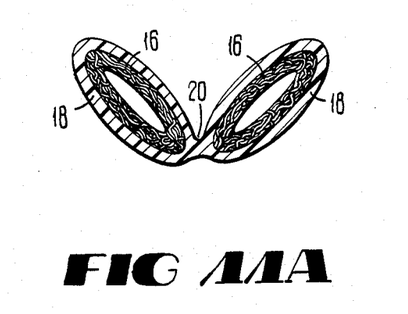
FIGS. 11A, 11B and 11C show the hinge effect in various positions formed by the fiber-rubber-fiber bonds of the tape substrate of the present invention.
Figure 11B:
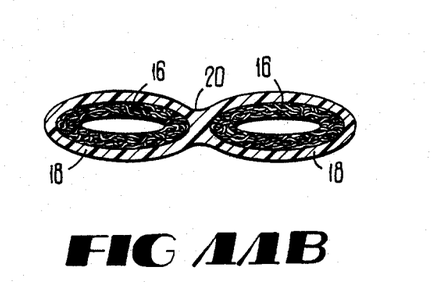
Figure 11C:
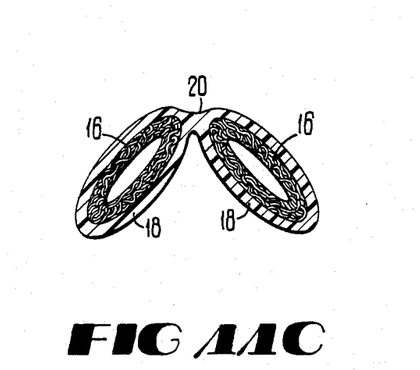

FIGS. 10 and 11 show the fibers 16 joined by a soft rubber-like polymer 18 to form the fiber-rubber-fiber bonds 20. As can be seen in cross-section in FIGS. 11A, 11B and 11C, the cellulose fibers 16 are coated with the soft rubber-like polymer 18 to form the bonds 20. These bonds are flexible, thereby allowing the fibers to pivot and move much like a hinge as shown by the varied positions of the fibers 16 in FIGS. 11A, 11B and 11C. The rubber bonds 20 will also stretch without breaking to distribute stresses in the tape substrate over a larger area in a manner similar to cloth.

Once the cellulose web 12 has been formed and saturated with a soft rubber-like polymer, thermoplastic coating 14 and 15 are extruded onto both sides of the web 12. The thermoplastic coatings 14 and 15 comprise a low-stiffness thermoplastic polymer. "Low-stiffness" means the polymer has a tensile modulus of less than 1,000 MPa and most preferred in the range of 50 to 150 MPa. Such tensile moduli are measured in accordance with ASTM Standard D-368. Low density polyethylene, ethylene vinyl acetate and polyethylene acrylic acid which are low stiffness are useful in carrying out the present invention. The thermoplastic coatings 14 and 15 are each extruded to coating thicknesses of between about 0.006 and about 0.050 mm. The thermoplastic coatings 14 and 15 impart some additional tensile strength to the substrate, but more importantly, one of the coatings such as coating 14 is then embossed with a fabric-like pattern 17 which imparts the impression that the substrate is cloth-like in nature. The other thermoplastic coating 15 provides an impervious surface onto which an adhesive may be coated when the substrate is ultimately converted to a tape. In some cases when an impervious surface is not needed for the adhesive, the coating 15 may be eliminated. Extrusion coatings are preferred because aqueous coating systems cause excessive penetration of the saturated web.

The following examples are illustrative of the prior art and the present invention:

EXAMPLE 1 (Prior Art)

| Conventional Tape Base for Diaper Application | |
| --- | --- |
| Unsaturated Base: | 100% northern softwood kraft, $R_{10}$ value of approximately 85 to 86. Breaking length of 3.5 to 4.0 km. Weight of unsaturated base: 90 g/m$^2$. |
| Latex Saturated Base (rubber saturated) | Soft polyacrylate polymer saturant with a Tg value of $-11°$ C. The amount of dry saturant add-on was 48 parts per 100 parts fiber. The resultant basis weight was 133 g/m$^2$. |
| Barrier Coating Formulation: | The latex saturated substrate was coated with a coating formulation containing equal parts of polyacrylate latex and TiO$_2$ pigment. The polyacrylate latex had a Tg value of 8° C. |
| Coat Weight: | 17 to 20 g/m$^2$ |
| Physical Properties | |
| Strip Tensile: | MD: 13 to 16 kg/25 mm CD: 11 to 14 14 kg/25 mm (TAPPI method T404-OS-61) |
| Stretch: | MD: 3 to 4% CD: 8 to 10% (TAPPI method T404-OS-61) |
| Gurley Stiffness: | MD: 370 to 400 mg. CD: 160 to 180 mg. |
| Basis weight: | 150–153 g/m$^2$ |

EXAMPLE 2

| Flexible Cloth-like Tape Backing. | |
| --- | --- |
| Unsaturated Base: | 25% softwood kraft with an $R_{10}$ value of 98.6% 75% softwood kraft with an $R_{10}$ value of approximately 88%. Breaking length of 2.66 km. Basis weight of 90 g/km$^2$. |
| Latex Saturated Base (rubber saturant) | Acrylonitrile butadiene stryene carboxylated polymer with a Tg of $-50°$ C. and TiO$^2$ pigment. The ratio of latex to pigment by weight was 3 to 1. The amount of dry saturant add-on was 60 parts per 100 parts fiber. The resulting basis weight was 144 g/m$^2$. The web was heat cured in an oven at 107° C. for four hours. |
| Coating: | The latex saturated substrate was extrusion coated on one side with a low density polyethylene acrylic acid co-polymer containing 3.5% acrylic acid monomer. The tensile modulus of the plastic was approximately 50 MPa. The coating thickness was 0.05 mm. |

The coated substrate was then calender embossed with a woven cloth pattern.

EXAMPLE 3

| Flexible Cloth-like Tape Backing. | |
| --- | --- |
| Unsaturated Base: | 50% soft wood kraft with an $R_{10}$ value of 98.6%. 50% soft wood kraft with an $R_{10}$ value of approximately 88%. Breaking length of 2.21 km. Basis weight of 110 g/m$^2$. |
| Latex Saturated Base (rubber-like saturant) | polyacrylate saturant (self curing with heat) with a Tg value of $-14°$ C. The amount of dry saturant add-on was 40 parts per 100 parts of fiber. The resulting basis weight was 154 g/m$^2$. The web was heat cured in an oven at 107° C. for four hours. |
| Coating: | The latex saturated substrate was extrusion coated on both sides with an ethylene vinylacetate copolymer. The tensile modulus of the polymer was about 80 MPa. The coating thickness was 0.0075 mm on each side. |

The coated substrate was then calender embossed with a woven cloth pattern.

EXAMPLE 4

| Flexible Cloth-like Tape Backing. | |
| --- | --- |
| Unsaturated Base: | 40% southern softwood kraft with an $R_{10}$ value of 98.6%. 40% western softwood sulfite with an $R_{10}$ value of 95.2%. 20% southern softwood kraft with an $R_{10}$ value of 87.0%. Breaking length of 0.89 km. Basis weight of 90 g/m$^2$. |
| Latex Saturated Base (rubber saturated | Acrylonitrile butadiene carboxylated polymer with a Tg of $-36°$ C. and a TiO$_2$ pigment. The ratio of latex to pigment by weight was 4 to 1. The amount of dry saturant add-on was 80 parts per 100 parts fiber. The resulting basis weight was 162 g/m$^2$. The web was heat cured in an oven at |

-continued

| Flexible Cloth-like Tape Backing. | |
|---|---|
| Coating: | 107° C. for four hours.<br>The latex saturated substrate was extrusion coated on both sides with a low density polyethylene polymer.<br>The tensile modulus of the plastic coating was 180 MPa.<br>The coating thickness was 0.013 mm on each side. |

The coated substrate was then calender embossed with a woven cloth pattern.

EXAMPLE 5

| Flexible Cloth-like Tape Backing. | |
|---|---|
| Unsaturated Base: | 100% softwood kraft with an $R_{10}$ value of 94 to 95%.<br>Breaking length of 1.77 km.<br>Basis weight of 90 g/m². |
| Latex Saturated Base (rubber-like saturant): | Styrene butadiene carboxylated polymer with a Tg of −31° C.<br>The saturant was made up of 3 parts latex and 1 part $TiO_2$ by weight.<br>The amount of dry saturant add-on was 50 parts per 100 parts fiber.<br>The resulting basis weight was 135 g/m².<br>The web was heat cured in an oven for one hour at 125° C. |
| Coating: | The latex saturated substrate was extrusion coated on one side with a plasticized polyvinyl chloride polymer.<br>The tensile modulus of the polymer was about 1000 MPa.<br>The coating thickness was 0.025 mm. |

The coated substrate was then calender embossed with a woven cloth pattern.

EXAMPLE 6

Flexible Cloth-like Tape Backing.

The unsaturated base web of Example 3 was used with the saturant and the amount of add-on being changed. The saturant polymer was a rubber-like polyacrylate with a Tg of about −4° C. The amount of dry polymer add-on was 50 parts per 100 parts fiber. No $TiO_2$ was added because of the good color stability of the polymer. In this case the saturated web was not heat cured. The coating and embossing were the same as Example 3.

REVIEW OF EXAMPLES 2-6

The useful strength of typical paper based tapes is measured by strip tensile in conjunction with stretch to the point of break as stated by Schmidt. In such cases there is a high degree of fiber-fiber bonds in the paper composite. As a result, the stress forces at the point of tear are distributed over only a very small area. In the case of this invention, the primary bonds are fiber-rubber-fiber. As a result, the stress forces are distributed over a much larger area and act more like a cloth-like fabric than paper. In such cases, a more meaningful test of useful strength and tear resistance is grab tensile. In the cases where the fiber-rubber-fiber bonds dominate, tape composites that have grab tensile of 10 kg or more are useful as diaper fasteners, even though if tested as paper tapes, the strip tensile may be lower than the 11 kg/25 mm as stated by Schmidt.

For examples 2 through 6, the grab tensile values using FTMS-191 A Method 5100 are in the range of:

MD: 16 to 24 kg.

CD: 11 to 17 kg.

The flexibility for these materials is measured by the Gurley stiffness and is in the range of:

MD: 100 to 180 mg.

CD: 80 to 150 mg.

As can be seen from the above data, all grab tensiles were greater than the required minimum of 10 kg. Also note that the stiffness values for the tape substrates of the present invention are much lower than that of the prior art Example 1, thereby indicating a greater flexibility for the tape substrate of the present invention.

We claim:

1. A flexible tape backing substrate comprising:
   (a) a cellulose web of pulp fibers with a breaking length between about 0.71 km and about 2.66 km in which at least 25% by weight of the fibers have $R_{10}$ values equal to or greater than 94%;
   (b) a soft rubber-like polymer having a glass-transition temperature of between about −50° C. and 0° C. bonding the fibers to each other to form fiber-rubber-fiber bonds within said web, said soft rubber-like polymer being present in said cellulose web to at least about 35 parts dry add-on to 100 parts fiber;
   (c) a coating of thermoplastic polymer with a tensile modulus of less than 1,000 MPa on the cellulose web; and
   (d) said substrate being embossed on at least one side with a fabric-like pattern.

2. The substrate of claim 1, wherein the coating is from about 0.006 mm to about 0.05 mm thick.

3. The substrate of claim 2, wherein the fibers having $R_{10}$ values equal to or greater than 94% comprise 50% to 100% by weight of the fibers in the web.

4. The substrate of claim 3, wherein the thermoplastic polymer has a tensile modulus of about 50 MPa to about 150 MPa.

5. The substrate of claim 4, wherein the breaking length of the cellulose web is between about 0.89 km and about 1.77 km.

6. The substrate of claim 5, wherein the thermoplastic polymer is selected from the group consisting of low density polyethylene, polyethylene vinyl acetate, polyethylene acrylic acid and copolymers of polyethylene.

7. The substrate of claim 6, wherein the soft rubber-like polymer is selected from the group consisting of natural rubber, nitrile rubber, styrene butadiene rubber, EPDM rubber, polyethylene vinyl acetates, and polyacrylates.

8. A flexible tape backing substrate comprising:
   (a) a cellulose web of substantially unbonded pulp fibers with a breaking length between 0.71 km and about 2.66 km in which at least 25% by weight of the fibers have $R_{10}$ values equal to or greater than 94%;
   (b) a soft rubber-like polymer having a glass-transition temperature of between about −50° C. and 0° C. bonding the fibers to each other to form fiber-rubber-fiber bonds within said web, said soft rubber-like polymer being present in said cellulose web to at least about 35 parts dry add-on to 100 parts fiber;

(c) a coating on said web of thermoplastic polymer with a tensile modulus of less than 1,000 MPa on the cellulose web; and (d) said substrate being embossed on at least one side with a fabric-like pattern.

9. The substrate of claim 8, wherein the coating is from about 0.006 mm to about 0.05 mm thick.

10. The substrate of claim 9, wherein the fibers having $R_{10}$ values equal to or greater than 94% comprise 50% to 100% by weight of the fibers in the web.

11. The substrate of claim 10, wherein the thermoplastic polymer has a tensile modulus of about 50 MPa to about 150 MPa.

12. The substrate of claim 11, wherein the breaking length of the cellulose web is between about 0.89 km to about 1.77 km.

13. The substrate of claim 12, wherein the thermoplastic polymer is selected from the group consisting of low density polyethylene, polyethylene vinyl acetate, polyethylene acrylic acid and copolymers of polyethylene.

14. The substrate of claim 13, wherein the soft rubber-like polymer is selected from the group consisting of natural rubber, nitrile rubber, styrene butadiene rubber, EPDM rubber, polyethylene vinyl acetates, and polyacrylates.

15. A method for making a flexible tape backing substrate comprising the steps of:

(a) forming a cellulse web with a breaking length between about 0.71 km and about 2.66 km, said cellulose web comprising at least 25% cellulose pulp fibers with $R_{10}$ values equal to or greater than 94% by weight;

(b) saturating the web with a soft rubber-like polymer to at least about 35 parts dry add-on of soft rubber-like polymer to 100 parts fiber to form fiber-rubber-fiber bonds within said web, said soft rubber-like polymer having a glass-transition temperature between about −50° C. and 0° C.;

(c) coating the web with a thermoplastic polymer having a tensile modulus less than 1,000 MPa; and (d) embossing said substrate on at least one side to form a cloth-like appearance.

16. The method of claim 15, wherein the coating has a thickness between about 0.0006 mm and about 0.05 mm.

17. The method of claim 16, wherein the fibers having $R_{10}$ values equal to or greater than 94% comprise 50% to 100% by weight of the fibers in the web.

18. The method of claim 17, wherein the thermoplastic polymer has a tensile modulus of 50 MPa to 150 MPa.

19. The method of claim 18, wherein the breaking length of the cellulose web is between about 0.89 km and about 1.77 km.

20. The method of claim 19, wherein the thermoplastic polymer is selected from the group consisting of low density polyethylene, polyethylene vinyl acetate, plyethylene acrylic acid and copolymers of polyethylene.

21. The method of claim 20, wherein the soft rubber-like polymer is selected from the group consisting of natural rubber, nitrile rubber, styrene butadiene rubber, EPDM rubber, polyethylene vinyl acetates, and polyacrylates.

* * * * *

UNITED STATES PATENT AND TRADEMARK OFFICE
CERTIFICATE OF CORRECTION

PATENT NO. : 4,837,070

DATED : June 6, 1989

INVENTOR(S) : Robert E. Weber and Bruce G. Stokes

It is certified that error appears in the above-identified patent and that said Letters Patent is hereby corrected as shown below:

Column 2, line 32, "fiber bond act" should read --fiber bonds act--.

Column 3, line 23, "thermoplastic coating" should read --thermoplastic coatings--.

Column 5, line 14, "coating 14 and 15" should read --coatings 14 and 15--.

Column 6, line 9, "stryene" should read --styrene--.

Column 6, line 63, "(rubber saturated)" should read --rubber saturated--.

Column 9, line 33, "cellulse" should read --cellulose--.

Column 10, line 28, "plyethylene" should read --polyethylene--.

Signed and Sealed this

Twenty-third Day of March, 1993

*Attest:*

STEPHEN G. KUNIN

*Attesting Officer*     Acting Commissioner of Patents and Trademarks